(12) United States Patent
Daunert et al.

(10) Patent No.: US 7,482,381 B2
(45) Date of Patent: Jan. 27, 2009

(54) ARTIFICIAL MUSCLE HYDROGEL BLENDS REVERSIBLY ELECTROACTUATED NEAR NEUTRAL PH, IMPLANTABLE ACTUATING DEVICES, AND METHODS USING THE SAME

(76) Inventors: Sylvia Daunert, 4804 Pleasant Lawn Way, Lexington, KY (US) 40515; Serban F. Peteu, 802 Cherry La., Apartment 106, East Lansing, MI (US) 48823-5543; Leonidas G. Bachas, 4804 Pleasant Lawn Way, Lexington, KY (US) 40515; Marc J. Madou, 10390 Pacific Center Ct., San Diego, CA (US) 92121; Elissavet Moschou, 3051 Kirklevington Dr., Apt. 66, Lextington, KY (US) 40517

( * ) Notice: Subject to any disclaimer, the term of this patent is extended or adjusted under 35 U.S.C. 154(b) by 833 days.

(21) Appl. No.: 10/803,985

(22) Filed: Mar. 19, 2004

(65) Prior Publication Data

US 2004/0182704 A1 Sep. 23, 2004

Related U.S. Application Data

(60) Provisional application No. 60/509,054, filed on Mar. 19, 2003.

(51) Int. Cl.
 *A61K 47/30* (2006.01)
 *A61K 47/00* (2006.01)
 *A61K 9/14* (2006.01)
 *A61F 13/00* (2006.01)

(52) U.S. Cl. .................... 514/772.3; 514/784; 424/422; 424/487

(58) Field of Classification Search ................. 424/422, 424/487, 514, 772.3, 784
See application file for complete search history.

(56) References Cited

U.S. PATENT DOCUMENTS

| 5,062,841 A | 11/1991 | Siegel |
| 2002/0013545 A1 | 1/2002 | Soltanpour et al. |

*Primary Examiner*—Raymond J Henley, III
(74) *Attorney, Agent, or Firm*—McDermott Will & Emery LLP

(57) ABSTRACT

A novel artificial muscle material and miniature valves and micropumps made therefrom are provided. The artificial muscle material bends reversibly when electroactuated by applying low voltage, in a wide pH range, even at that of physiological pH, and works without contact with electrodes. Miniature valves made from the artificial material are successfully triggered for the fluid release in a wide pH range, even at that of physiological pH. Novel fluid release devices were manufactured using this artificial muscle, and methods using the same were provided, including an implantable device optimized for trans-scleral drug delivery.

17 Claims, 12 Drawing Sheets

(A)

(B)

(C)

(D)

ARTIFICIAL MUSCLE HYDROGEL BLENDS REVERSIBLY ELECTROACTUATED NEAR NEUTRAL PH, IMPLANTABLE ACTUATING DEVICES, AND METHODS USING THE SAME

This application claims priority from U.S. Provisional Patent Application No. 60/509,054, filed on Mar. 19, 2003.

FIELD OF THE INVENTION

The present invention relates generally to the controlled release of molecules, and to artificial muscle-type hydrogel and polymer blends, also called "artificial muscles", useful in controlled electro-responsive release of macromolecules. More particularly, the invention relates to actuating or drug delivery devices containing an artificial muscle valve and micropump that controls the release of therapeutic fluids—including implantable platforms—and specific methods using these artificial muscle-powered actuating devices.

BACKGROUND OF THE INVENTION

There are several publications related to environment-sensitive polymers and hydrogel blends, also called artificial muscles, including their application to actuating devices and drug delivery platforms. An artificial muscle is a polymer blend structured in a hydrogel network that changes its dimensions—that is deforms (e.g., swells, elongates or bends)—under the application of an environmental stimulus, e.g., pH, temperature or ionic strength gradient.

There are several patents presenting temperature-sensitive or pH-sensitive artificial muscle blends and related actuating or drug delivery devices. For example, Y. H. Bae et al. (1993) claim a pulsatile drug delivery device in U.S. Pat. No. 4,927,632. Similarly, A. Zirino (1994) claims in U.S. Pat. No. 5,334,629 the reversible controlled activation of pH-dependent fibers and gels. Also, in U.S. Pat. No. 5,904,927, M. M. Amiji (1999) synthesized a semi-interpenetrating network pH-sensitive hydrogel used for drug delivery. Unfortunately, all these and other temperature-sensitive or pH-sensitive polymer-hydrogel blends have a drastically limited use in-vivo. This is because this type of hydrogels is not selective, but rather, generally responds to any pH or temperature change occurring by any abnormality in the organism. Furthermore, in general—with very few exceptions, like that of pH gradient in the human digestive tract—one cannot create ad-hoc, or take advantage of, a natural temperature gradient or pH gradient in close proximity, or inside a living mammalian organism without risks of causing severe discomfort. In addition, there is a great need for generic drug release devices that meet each patient's needs by offering individualized therapy.

Another group of patents illustrates electro-sensitive artificial muscle blends and related actuating or drug delivery devices. For example, M. Shahinpoor (1995) outlines spring-loaded electrically controlled polymeric actuators, working in an electrolytic bath, such as a water-acetone solution, in the U.S. Pat. No. 5,389,222. Unfortunately, there is a real toxicity risk involved in using acetone solutions in proximity of living tissues, so the possibility of acetone leakage makes these gels unusable in-vivo. Also, M. Shahinpoor and K. J. Kim (2002) disclose a dry electroactive polymeric muscle in US 2002/0050454US (published patent application). Their purpose is to manufacture artificial muscles that work in dry environments, which makes them in general unusable in-vivo. M. Shahinpoor and K. J. Kim (2002) also outline novel metal hydride artificial muscles operated both electrically and thermally, for extra-corporeal, robotic, space and defense applications, including micromachines in their US published patent application 2002/0026794. Clearly, using hydrogen gas as a working fluid stored interstitially in metal hybrids is definitely not an option for artificial muscles used in direct proximity of living tissues, due to the extremely high risks involved. R. E. Pelrine and R. D. Kornbluh (2002) presented electroactive gels actuated with voltages in the order of mega-volts/meter (U.S. Pat. No. 6,376,971). These extremely high voltages cannot be used in proximity of living tissues.

In terms of actuating or drug delivery devices per se, there are for example the microelectrochemical valve patented by M. J. Madou and M. J. Tierney (1994, U.S. Pat. No. 5,364,704) and the microchip drug delivery device of J. T. Santini et al. (1998, U.S. Pat. No. 6,123,861), both using the concept of a sacrificial valve: the electrochemical dissolution of a cover metal film that seals the microreservoir containing a therapeutic agent. However generic and potentially implantable, this design is for single use—that is, when a sacrificial valve is opened to release the content of the microreservoir/valve cannot be used again to deliver another dose of therapeutic agent.

Other electroactuated delivery devices use electrolytic cells for generating a controlled quantity of gas, thus causing displacement of an interface or piston that allows release of a material. For example, C. R. Bunt et al (2002, U.S. Pat. No. 6,450,991) designed such a device for intra-ruminal use.

There are also pumps and actuating devices using electro-actuating polymers. For example, a synthetic muscle-based diaphragm pump is disclosed by D. Soltanpour and M. Shahinpoor (2002) in their published patent application 2002/0013545, based on the ionic polymer conductor composite polymer developed by Shahinpoor et al. However, no actuating parameters (voltage, current) and no testing data are provided.

In other cases, implantable pumps use an aqueous swellable hydrogel blend. Some publications describe continuous drug release due to an osmotic gradient through a membrane of predetermined porosity, for example the Duros implant system by J. C. Wright et al. (Journal of Controlled Release, 2001, 46, 125-148). An inherent limitation of these systems is the passive, and continuous release of the drug at a pre-determined rate.

Other release platforms are activated by hydrogels responsive to a specific chemical in the body. An example is the implantable self-regulating mechano-chemical insulin pump, by R. A. Siegel (1989, U.S. Pat. No. 5,062,841), working as a pH-sensitive gel, responsive to the pH local change generated by the oxidation of glucose to gluconic acid, biocatalyzed by the enzyme glucose oxidase immobilized in the gel network. The limitations using this approach include the available oxygen level in vivo, and the hydrogel reproducibility and lifetime. Another inconvenience is that this design is by definition limited in scope, and cannot provide a generic platform usable for all therapeutic agents.

In general, the above examples show that there is little effort devoted to the design of a generic electroactuated drug release system, which will operate at physiological pH and be able to provide adjustable drug release for personalized therapy. Thus, there is a real need for fast-acting electroactive reversible artificial muscle that will function at a wide range of pH, even at near neutral pH, and which can be configured to any desired geometry for use as an actuator in implantable drug delivery devices.

SUMMARY OF THE INVENTION

In one aspect of the invention there is provided an electroactive artificial muscle, comprising a hydrogel comprising acrylamide; an unsaturated aliphatic acid having the formula R=CH—COOH, wherein R is selected from the group consisting of —$CH_2$, —CH—COOH, and —CH—$(CH_2)_n$—COOH, where n is an integer; a composite of a conductive polymer such as polypyrrole-carbon black, and at least one cross-linking agent, wherein the hydrogel is electroactive at a wide pH range, even at that of physiological pH, and in the absence of contact with the electrodes. In a preferred embodiment the unsaturated aliphatic acid is acrylic acid, maleic acid or glutaconic acid, or combinations of the above. In another preferred embodiment the acrylic acid, maleic acid, glutaconic acid, or their combination is present in the hydrogel precursor solution in an amount of about 65 wt %.

In another aspect of the invention, there is provided an actuating device or drug delivery device for controlled release of a therapeutic, prophylactic or diagnostic agent to an animal, comprising an electroactive artificial muscle, comprising a hydrogel comprising acrylamide; an unsaturated aliphatic acid having the formula R=CH—COOH, wherein R is selected from the group consisting of —$CH_2$, —CH—COOH, and —CH—$(CH_2)_n$—COOH with n being an integer; a composite of a conductive polymer such as polypyrrole-carbon black; and at least one cross-linking agent; wherein the hydrogel is electroactive at physiological pH and in the absence of contact with electrodes under the application of an electric field, preferably 1-4.5 V, with a current intensity preferably of 0.01-1 A, and wherein the artificial muscle electroactuation opens an enclosure (normally closed by the non actuated hydrogel), thus releasing the therapeutic, prophylactic or diagnostic agent from the drug delivery device.

In yet another aspect of the invention, there is provided an actuating or drug delivery device for the controlled release of a therapeutic, prophylactic or diagnostic agent to an animal, comprising an electroactive artificial muscle comprising acrylamide; an unsaturated aliphatic acid having the formula R=CH—COOH, wherein R is selected from the group consisting of —$CH_2$, —CH—COOH, and —CH—$(CH_2)_n$—COOH with n being an integer; a composite of a conductive polymer such as polypyrrole-carbon black; and at least one cross-linking agent, wherein the hydrogel is electroactive at physiological pH and in the absence of contact with electrodes under the application of an electric field, preferably 1-4.5 V, with a current intensity preferably of 0.01-1A, and wherein the electroactuated artificial muscle applies controlled mechanical force onto the wall of a flexible reservoir, releasing the therapeutic, prophylactic or diagnostic agent from the drug delivery device. In another preferred embodiment, the wall of the flexible reservoir comprises at least one portion of the artificial muscle.

In yet another aspect of the invention, there is provided an actuating or drug delivery device for the controlled release of a therapeutic, prophylactic or diagnostic agent to an animal, comprising an electroactive artificial muscle comprising acrylamide; an unsaturated aliphatic acid having the formula R=CH—COOH, wherein R is selected from the group consisting of —$CH_2$, —CH—COOH, and —CH—$(CH_2)_n$—COOH with n being an integer; a composite of a conductive polymer such as polypyrrole-carbon black; and at least one cross-linking agent. Such a hydrogel is electroactive in a wide pH range, even at that of physiological pH and in the absence of contact with electrodes under the application of an electric field, preferably of 1-4.5 V, with a current intensity preferably of 0.01-1 A, wherein an artificial muscle-based super-flexible bladder equipped with a one-way minivalve is optimized for implantable drug release.

In another aspect of the invention, there is provided a method for delivering a therapeutic, prophylactic or diagnostic agent to a patient comprising implanting in the body of the patient or applying to the body of a patient an actuating or drug delivery device comprising an electroactive artificial muscle comprising a hydrogel comprising acrylamide; an unsaturated aliphatic acid having the formula R=CH—COOH, wherein R is selected from the group consisting of —$CH_2$, —CH—COOH, and —CH—$(CH_2)_n$—COOH with n being an integer; a composite of a conductive polymer; and at least one cross-linking agent, wherein the hydrogel is electroactive at physiological. pH and in the absence of contact with electrodes under the application of an electric field, and wherein the electroactive artificial muscle applies controlled mechanical force onto the wall of a flexible reservoir of the device, releasing the therapeutic, prophylactic or diagnostic agent from the device.

BRIEF DESCRIPTION OF THE DRAWINGS

In FIG. 8C the way of determining the bending angle, θ, which is used to express the response of the muscle [according to the formula $\theta = 2 \tan^{-1}(y/x)$] is shown.

In FIG. 9C the volume of the fluid release as a function of time, as determined using a pattern recognition shareware software (posted on the internet by the University of Texas Health Science Service at San Antonio Tex.).

In FIG. 10B the bending of the artificial muscle as a function of time altering the actuation potential is shown.

DETAILED DESCRIPTION OF THE INVENTION

Figure 1:
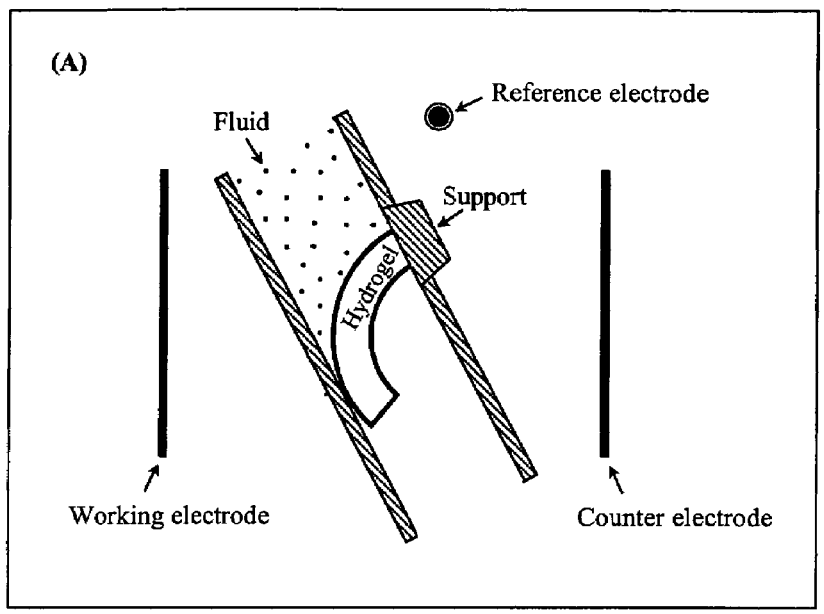
FIG. 1. The application of the artificial muscle in a flap valve-type configuration is demonstrated. The artificial muscle is positioned in a flow channel with one side fixed on the wall of the tube, and another side resting free, slightly bent, on the tube's inner wall. The artificial muscle is placed between two Pt electrodes using a Ag/AgCl reference electrode and the whole setup is immersed in the test solution of 150 mM NaCl. When no potential is applied, the flap valve is fully closed, so when the top of the tube is filled with fluid the muscle prevents the liquid to flow through the tube (FIG. 1A). Under the application of an electric field the artificial muscle bends toward the cathode, opening the channel and permitting the flow of fluid (FIG. 1B).
Figure 1:
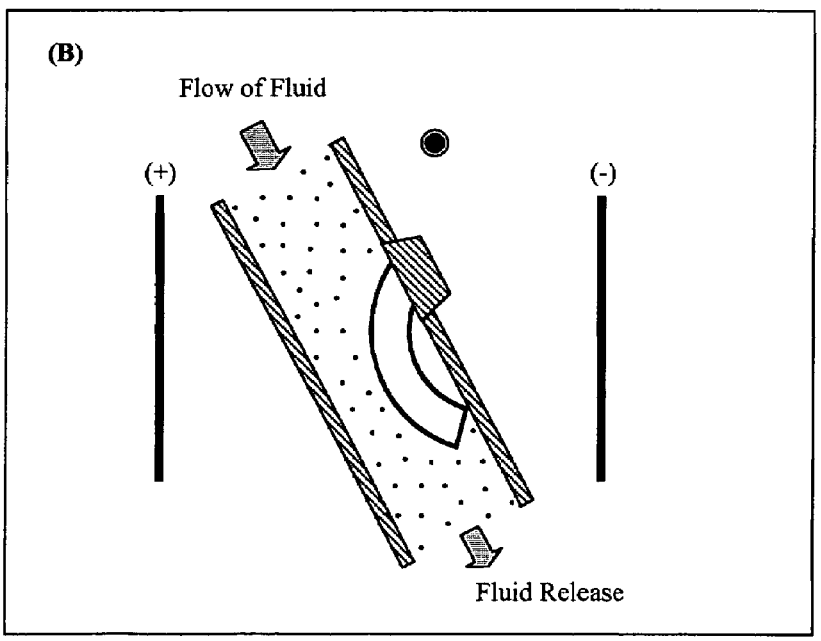

The present invention is directed to a novel hydrogel composite for use as an artificial muscle. The artificial muscle contains an unsaturated aliphatic acid of the general formula R=CH—COOH, where R is selected from —$CH_2$, —CH—COOH, or —CH—$(CH_2)_n$—COOH, where n is an integer, such as for example, acrylic acid ($H_2C$=CH—COOH), maleic acid (HOOC—CH=CH—COOH) or glutaconic acid (HOOC—$CH_2$—CH=CH—COOH), or a combination thereof; acrylamide; and a composite of a conductive polymer, such as, for example, polypyrrole-carbon black (PPy/CB) (defined herein as a mixture of polypyrrole doped with carbon black, preferably having a ratio of polypyrrole to carbon black of 5:1), polythiophene-carbon black, polyaniline-carbon black, polypyrrole-carbon fibers, polythiophene-carbon fibers or polyaniline-carbon fibers. The artificial muscle of the invention provides rapid, reversible bending under the application of low voltage in solutions of wide pH range, e.g., from about pH 3 to about pH 10, including physiological pH. By low voltage is meant about 1 to about 5 V, preferably about 1 to about 2 V. The artificial muscle of the invention is particularly suited for microfabrication of electro-sensitive soft microvalves and micropumps for use in biomedical and other applications, such as, for example, the manufacture of artificial muscle valves that may be used externally or as implantable devices.

The ability of the artificial muscle of the invention to bend and the obtained response in terms of bending angle, depend on the chemical composition of the hydrogel precursor solution used for the polymerization of the artificial muscle. In general, the higher is the aliphatic acid content of the hydrogel, the higher is the bending angle of the material that can be achieved. Therefore, increase of the aliphatic acid content in the hydrogel precursor solution results in the increase of the artificial muscle response (for example, the increase in the acrylic acid content of a hydrogel from 45 wt. % to 57 wt. % and then to 65 wt. % results in the increase of the bending angle of the resulting hydrogel to 6.9°, 11.4° and 15.0°, respectively under electroactuation at 3 V with a response time of 2 min). Further increase in the aliphatic acid content generally increases the hydrogel response at the expense of mechanical stability of the artificial muscle. Therefore, it is preferable that the hydrogel contains about 65 wt. % aliphatic acid as defined herein, although the amount can vary depending on the intended use of the artificial muscle, in terms of response, response time and lifetime of the material.

The response of the hydrogel is also affected by the number of COOH groups of the unsaturated aliphatic acid monomer used in the hydrogel precursor solution. In this regard, the selected unsaturated aliphatic acid may be a single unsaturated aliphatic acid with one carboxylic group, such as acrylic acid, or more carboxylic acids, like maleic acid or glutaconic acid, or even a mixture of unsaturated aliphatic acids may be used to provide the desired amount of COOH groups and hence elasticity and response of the artificial muscle. It was seen that the response of a hydrogel based on a 65 wt. % aliphatic acid content increases when using maleic acid (which. incorporates two carboxylic groups per molecule of monomer with molecular weight 116.07), to glutaconic acid (with two carboxylic groups per monomer molecule of molecular weight 130.10) to finally acrylic acid (with one carboxylic group per monomer molecule of molecular weight 72.06).

Further optimization of the artificial muscle composition of the invention is based on the use of a composite of a conductive polymer, such as the polypyrrole/carbon black composite (PPy/CB) as an additive. The high conductivity of this composite results in an increase in the conductivity of the composition, enhancing the hydrogel electroactuation. It was seen that the degree of bending of a hydrogel containing 4 wt. % PPy/CB (polypyrrole doped with 20% carbon black) is higher (23.5° bending angle) than that of a hydrogel containing 1 wt. % PPy/CB, (15.0° bending angle). In addition, a hydrogel containing 4 wt. % carbon black alone presents a significantly lower response (15.8° bending angle) than the 4 wt. % PPy/CB counterpart. The response of a blank artificial muscle without any PPy/CB additive is significantly less, with a respective bending angle of 10.3°, verifying the positive effect of the PPy/CB composite on the hydrogel electroactuation of the artificial muscle of the invention.

The effect of the electric field on the electroactuation of the artificial muscle of the invention was also examined. For example, the bending angle of an artificial muscle, based on 65 wt. % acrylic acid and 4 wt. % polypyrrole/carbon-black, under the application of 3V at 1 cm distance from each Pt electrode is 23.5° in about two minutes. Decreasing the distance of the artificial muscle from each electrode to 0.5 cm results in the decrease of the response time of the artificial muscle to 30 seconds and an increase of the bending angle to 28°. Conversely, an increase of the distance of the artificial muscle from each electrode results in a decreased response (e.g., 2° under the application of 3V under the same period of two minutes) of the material.

The supporting electrolyte concentration also has an effect on the artificial muscle response time. For example, an artificial muscle based on a hydrogel composition containing 65 wt. % acrylic acid and 4 wt. % polypyrrole/carbon black (5:1) does not respond to the application of 3V under a period of two minutes when the electrolyte concentration is decreased by four orders of magnitude from 0.15 M to $0.15 \times 10^{-4}$ M NaCl (the same hydrogel presents a bending angle of 23.5° degrees under electroactuation with the same conditions in a 0.15 M NaCl test solution). A decrease in the intensity of the electric field (from 3V to 1V) results in an increase of the response time of the material (from 2 to 15 minutes).

The mechanism of deformation of the artificial muscle of the invention can be explained by the theory of the osmotic pressure in polymer networks, introduced by Flory (P. J. Flory, *Principles of Polymer Science*, Cornell Univ. Press, Ithaca, N.Y., 1953) and updated by Tanaka (Tanaka et al., Science, 1982, 218, 467). When a DC electric field is applied, the electrophoretic movement of ions results in an ion concentration gradient at the interfaces of the hydrogel with the test solution, resulting in the bending of the hydrogel toward the cathode. The bending angle of the artificial muscle depends on the electric field intensity, the local pH change, the sample dimensions, its relative proximity to the electrodes and the electrolyte ionic strength.

The response time of the artificial muscle of the invention depends on several factors, including the elasticity of the material, the dimensions of the artificial muscle, and the intensity of the electric field applied. If a faster response time is desired, a more elastic material may be synthesized. This may be achieved, for example by using less cross-linker or by selecting the unsaturated aliphatic acid to provide more elasticity. However, an increase in elasticity is generally accompanied by a decrease in mechanical stability for long-term use of the artificial muscle.

The artificial muscle material of the invention exhibits fast and reversible bending under electroactuation with a low applied voltage, in the range of about 1 to about 5 V, preferably in the range of from about 1 to about 2 V, in solutions of a wide pH range, even at that of physiological pH. This artificial muscle composition is readily applicable for use as an electroactuated micropump or microvalve, for example, for in vivo responsive drug delivery.

In general, the hydrogel precursor solution used for the preparation of the artificial muscles of the invention is prepared by mixing each of the components in the desired amount of water, preferably deionized water. The composite of the conductive polymer, most preferably a premix of polypyrrole and carbon black, preferably in a ratio of about 5 to 1, is dispersed in deionized water under sonication, for example. The desired amount of monomers of acrylamide, N,N'-methylenebisacrylamide and the desired combination of one or more unsaturated aliphatic acids are added to the premix of polypyrrole/carbon black solution and mixed to ensure thorough blending. The amount of unsaturated aliphatic acid(s) used is preferably in the range of about 25 to 75 wt. %, and most preferably about 65 wt. %; the content of acrylamide is preferably about 0.6 to about 20 wt. %, most preferably 6 wt. %; and the amount of N,N'-methylenebisacrylamide is preferably about 2 to 50 wt. %, most preferably 20 wt. %. Catalysts, such as potassium persulfate, sodium metabisulfite, and accelerators, such as TEMED (N,N,N,N-tetramethylethylenediamine), are added in the hydrogel precursor solution after the thorough mixing and degassing of the solution with nitrogen, for the removal of molecular oxygen.

When the hydrogel precursor solution is thoroughly mixed it is placed in an appropriate mold with the desired shape and dimensions and is cured by heating, for example at a temperature in the range of about 25° to about 140° C., preferably about 50° to about 60° C. The cured hydrogels may be stored in a saline solution, for example in a 0.15 M NaCl solution, for later use.

In one aspect of the invention, the hydrogel precursor solution may contain the desired amount of a therapeutic or prophylactic agent, such as for example, an antimicrobial agent, pharmaceutical agent, therapeutic protein, cells, nucleic acid, and the like. During the polymerization procedure of the hydrogel, the therapeutic agent is entrapped inside the hydrogel. Therefore, the hydrogel prepared by this manner can be used for the passive release of the therapeutic or prophylactic agent, based solely on the diffusion of the drug, or in the case of charged therapeutic or prophylactic agents, the release of the drug at higher rates can be aided by migration under the electroactuation of the hydrogel. The amount and type of therapeutic or prophylactic agent loaded into the artificial muscle depends on the intended use of the material and can be readily ascertained by the skilled practitioner.

In another aspect of the invention, the cured and shaped artificial muscle is operatively connected to a reservoir or multiple reservoirs containing the therapeutic agent(s) or prophylactic agent(s). The hydrogel, which is placed between the electrode plates, can rest on the top of a reservoir(s) filled with fluid. Under no electroactuation, the hydrogel seals the opening of the reservoir and inhibits the release of the therapeutic or prophylactic agent to the environment. When an electric field is applied, the hydrogel bends towards the cathode, uncovering the opening of the reservoir, and therefore allowing the therapeutic or prophylactic agent(s) to diffuse into the surrounding tissue or blood. Thus, electroactuation of the artificial muscle is used to open and close the reservoir(s), allowing the delivery of therapeutic or prophylactic agent(s). Preferably, an electric field of from about 1 to about 5 V is applied and preferably a current of 40 mA or less is generated. The electric field can be applied at a predetermined cycle of positive and negative voltage to effect an oscillating motion of the device of the artificial muscle.

The therapeutic agent used in combination with the artificial muscle can be for example, a local anaesthetic, e.g., lidocaine; antibiotic or anti-bacterial agent, e.g., penicillin or streptomycin; peptides or proteins, such as insulin; vasodilators; steroids; beta-blockers; a diagnostic agent, and the like. It is also possible to deliver more than one drug at a time, either as a mixture or from separate reservoirs, for example.

The artificial muscle of the invention can be formed in any desired configuration, dimensions and shape, such as for example, a flap valve. FIG. 1A illustrates an embodiment of the invention in which the artificial muscle is positioned in a flow channel. When immersed in a 150 mM NaCl aqueous solution and exposed to a DC electric field, for example +3 V, this flap valve bends toward the cathode, opening the channel and allowing the release and flow of the fluid within the channel (FIG. 1B). When the polarity of the electrodes is changed, the artificial muscle flips back to its original position, blocking the channel and stopping the release of the fluid in the channel.

Figure 2:
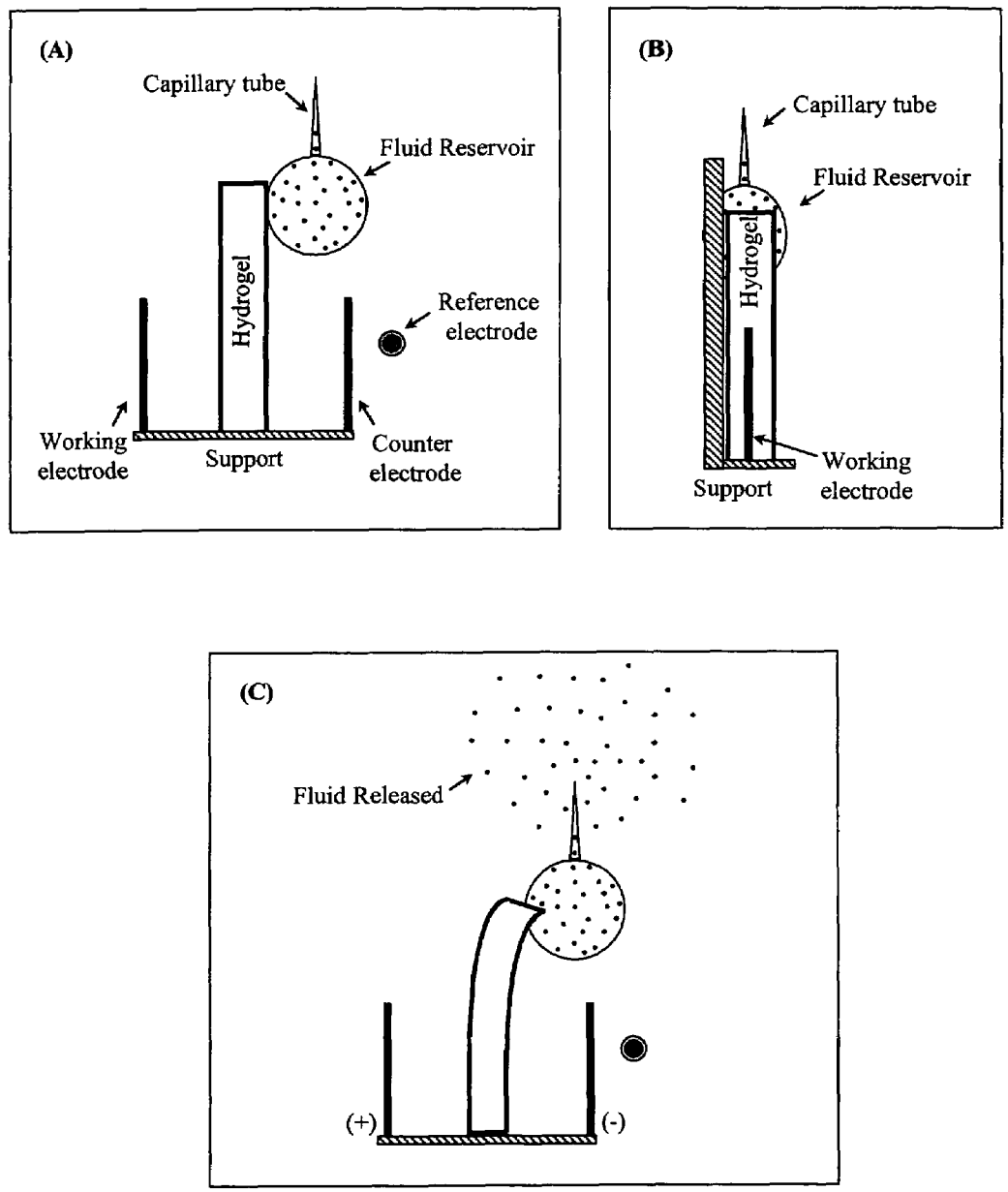
FIG. 2. A configuration in which a cylindrical artificial muscle is connected to a flexible semi-spherical reservoir is presented. The artificial muscle is fixed at one end on a support with its flat surface resting in the immediate vicinity of a semi-spherical latex reservoir (FIG. 2A,B top and side view). A micropipette tip is fixed at the end of a reservoir, which is filled with fluid. The muscle is placed between two Pt electrodes using a Ag/AgCl reference electrode, while the whole setup is immersed in the test solution of 150 mM NaCl. When no voltage is applied, the artificial muscle rests next to the reservoir and no fluid leakage is observed (FIG. 2A). Under electroactuation, the muscle bends toward the cathode, pressing the semi-spherical flexible reservoir, and thereby releasing the fluid contained within the reservoir (FIG. 2C).

FIG. 2A,B illustrates another configuration in which a cylindrical artificial muscle is connected to a flexible semi-spherical reservoir. When a voltage is applied, e.g., +3 V, the artificial muscle bends toward the cathode, and in the process pushes onto the semi-spherical flexible reservoir, thereby releasing some of the fluid contained within the reservoir (FIG. 2C).

Figure 3:
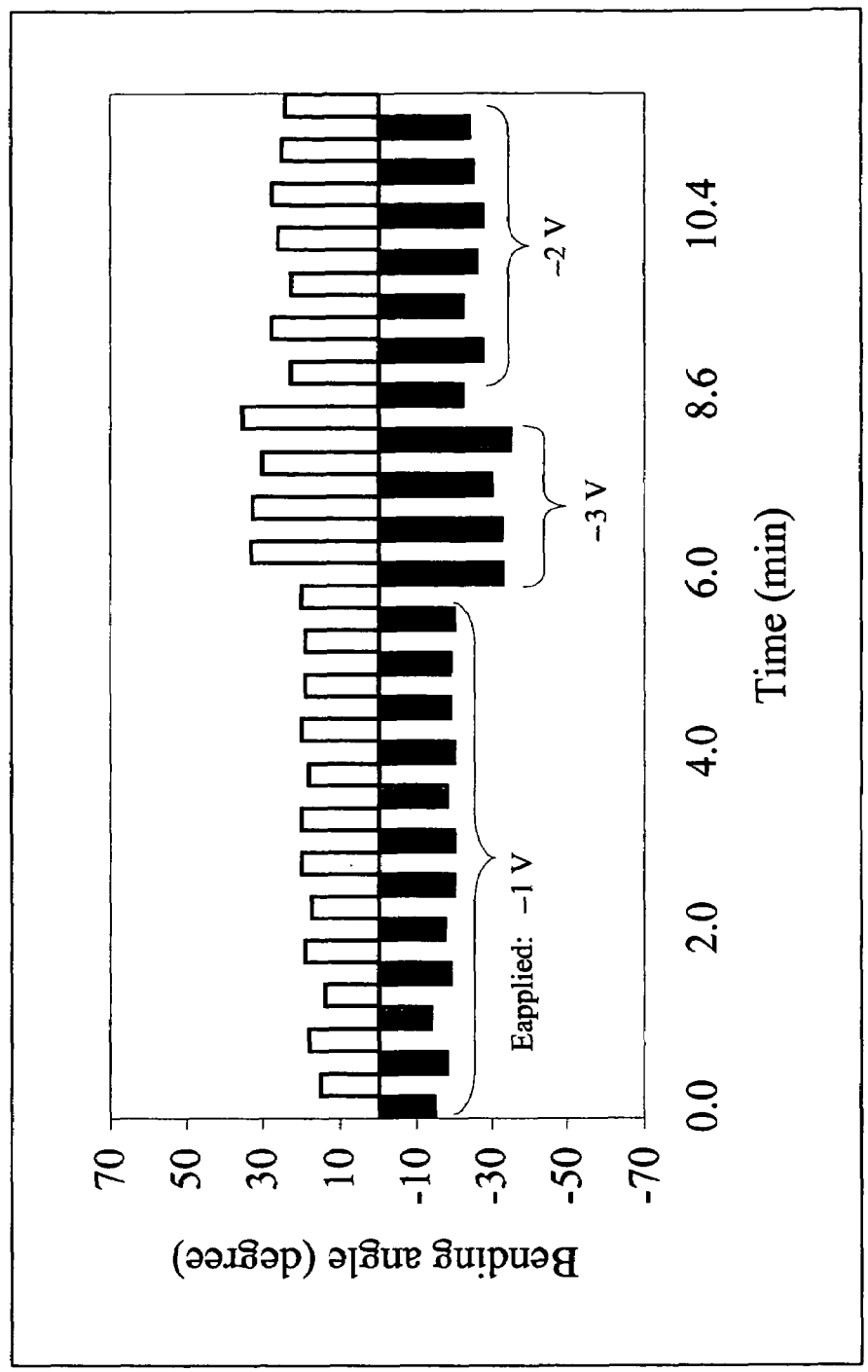
FIG. 3. The fast and reversible bending of a micromuscle configuration under the application of +/−1, 2 and 3 V is illustrated. The artificial muscle formed in a quasi-rectangular shape is partially attached to a support so that half of its length is free to move under the application of the electric stimuli. The artificial muscle is placed between two gold electrode plates using a Ag/AgCl reference electrode. The whole setup is immersed in the test solution of 150 mM NaCl. The application of the cycled voltage resulted in the bending of the artificial muscle in tune with the current wave presenting the response of 18°, 25° and 32° for the applied potentials of +/−1 V, 2 V and 3 V, respectively. The application of negative potentials (gray bars) results in bending of the hydrogel towards the opposite direction (denoted by the negative bending angles) than that when positive potentials (white bars) are applied (denoted by the positive bending angles).

The degree of bending and the response time of the artificial muscle under the application of an electric field can be tuned by altering the size dimensions of the muscle. FIG. 3 illustrates the fast and reversible bending of a micromuscle configuration under the application of various potentials. The artificial muscle is formed in a quasi-rectangular shape and is partially attached to a support so that half of its length was free to move under the application of the electric stimuli. The support with the attached artificial muscle is immersed in the electrochemical cell filled with 150 mM NaCl and placed between two gold electrode plates, under a microscope. Application of the cycled −1/+1 V voltage resulted in the bending of the artificial muscle in tune with the current wave presenting the response of 18° bending angle. The increase in the magnitude of the applied potential to 2 and 3 V results in the increase of the bending angle muscle to 25° and 32°, respectively. It should also be noted that the characteristics of the artificial micromuscle (bending angle and response time) are improved compared to an artificial macromuscle of the same composition and dimensions of 4×10 mm, with bending angle of 23.5° degrees under the application of 3 V for 2 min.

Figure 4:
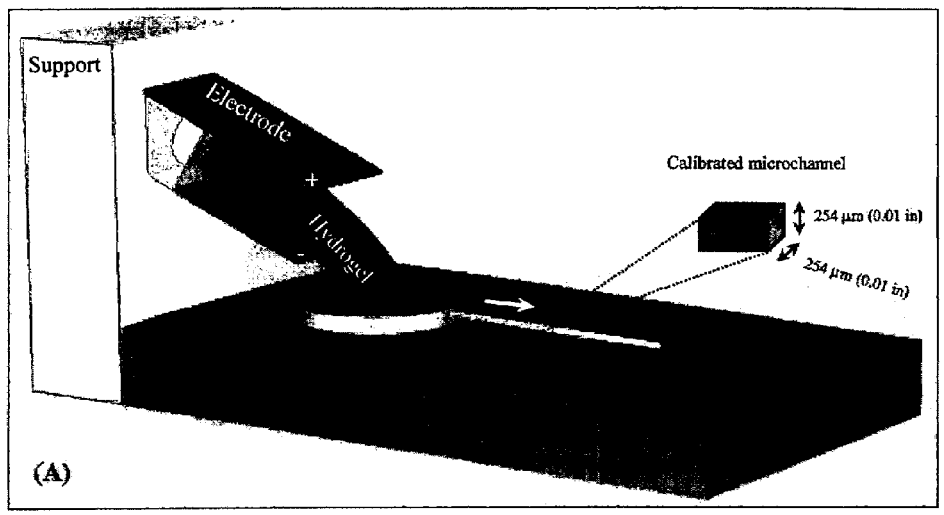
FIG. 4. An artificial muscle sample is used for the nanoliter- and microliter-range fluid release acting as a micropump. The artificial muscle is immersed in the test solution of 0.15 M NaCl, with the one end fixed on a support, and the other end placed on the surface of the mini-reservoir filled with fluid and covered with a poly(dimethylsiloxane) membrane. The end of the reservoir is connected to a calibrated polymethylmethacrylate microchannel of dimensions 254× 254 µm (FIG. 4A). Under electroactuation, the muscle bends and gently presses the flexible membrane that covers the reservoir, releasing fluid into the calibrated microchannel. Each electroactuation of the muscle results in the increase of the volume of the fluid released, while no fluid release is observed when no potential is applied (FIG. 4B).
Figure 4:
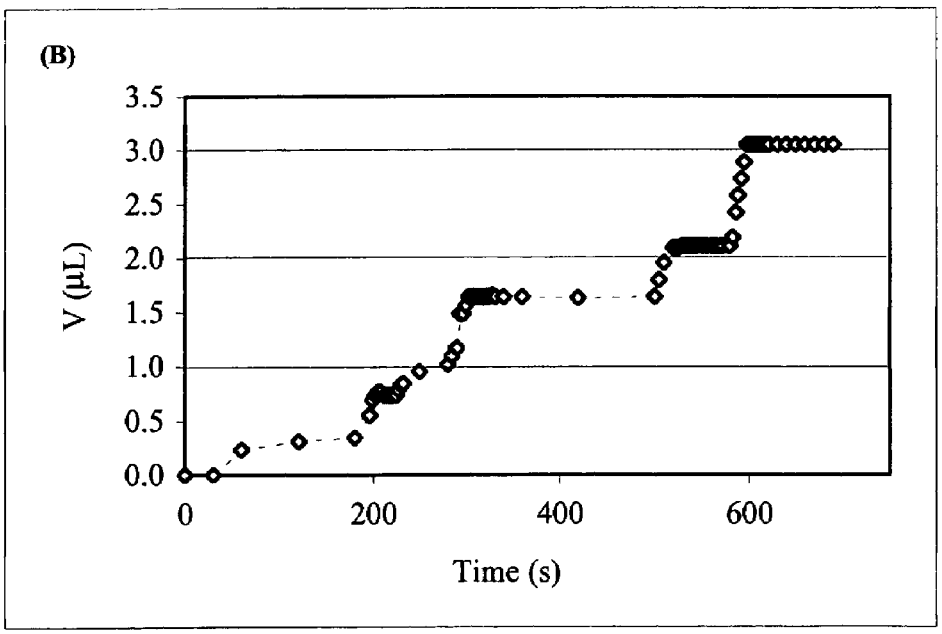

The artificial muscle may also lie on the top of a reservoir filled with fluid and covered by a soft membrane, preferably biocompatible, such as a silicone rubber membrane (FIG. 4A). The end of the reservoir is connected to a calibrated microchannel. When the artificial muscle is electroactuated it gently presses against the membrane, resulting in the release of the fluid from the reservoir into the microchannel. In FIG. 4B, the volume of the fluid released, which is in the order of microliters, by each electroactuation of the muscle is shown as a function of time. FIG. 4B demonstrates the ability of controlling the fluid release caused by each pulse of electroactuation by 4 V, while no fluid release is observed during the quiet time between the pulses when no potential is applied. The size and shape of the reservoir, and the material of the membrane may be varied depending on the desired application. The body of the reservoir can also be formed by any material, preferably biocompatible, such as silicone.

Figure 5:
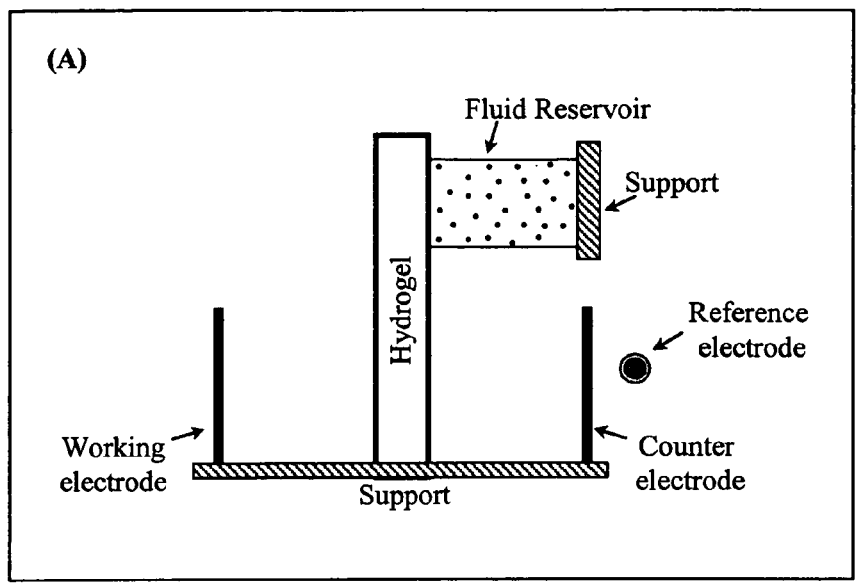
FIG. 5. A configuration in which a cylindrical artificial muscle is controlling fluid release by covering or exposing the opening of a reservoir filled with fluid. The artificial muscle is fixed at one end on a support between two Pt electrodes and a Ag/AgCl is used as the reference electrode. The flat surface of the muscle rests on and fully covers the opening of a reservoir filled with fluid. The whole setup is immersed in the test solution of 150 mM NaCl. When the artificial muscle is not electroactuated it blocks the opening of the reservoir, trapping the fluid inside the reservoir (FIG. 5A). The application of an electric filed actuates the muscle, which is now bending exposing the opening of the reservoir and permitting the release of the fluid in the environment (FIG. 5B).
Figure 5:
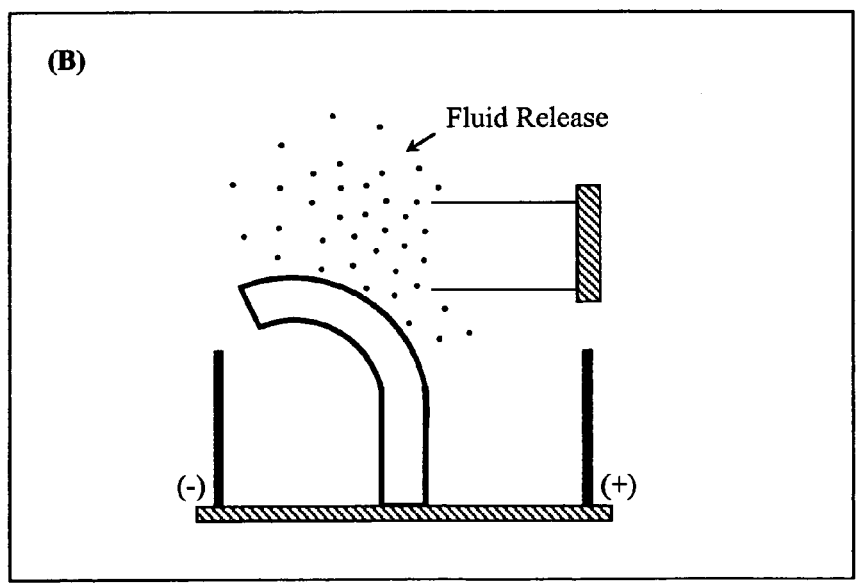

FIG. 5 illustrates another embodiment of the invention where the artificial muscle is covering the opening of a reservoir filled with fluid. When the artificial muscle is not electroactuated it blocks the opening of the reservoir, trapping the fluid inside the reservoir (FIG. 5A). The application of an electric field actuates the muscle, which is now bending exposing the opening of the reservoir and permitting the release of the fluid to the environment (FIG. 5B).

For transdermal therapy, the artificial muscle device, such as any of the devices containing a reservoir(s) described above, may also have an adhesive layer, which may be covered with tape or other suitable covering. After the covering tape is removed, the artificial muscle device is attached to the skin. The adhesive layer may contain one or more penetration enhancers to reduce the resistance of the skin.

The artificial muscle is preferably linked to an electric energy source such as a battery, for example, which provides a low voltage sufficient to actuate the muscle, e.g., preferably less than 4 V, more preferably between 1 and 3 V, and most preferably about 1.0 V. In a preferred embodiment of the invention, the battery cycles at a predetermined time to provide the controlled timed release of a drug or other agent.

The artificial muscle devices of the invention can be placed in suitable biocompatible housing for implantation at the desired site, such as for example, in close proximity to the coronary artery or the eye for trans-scleral drug delivery.

The artificial muscle material of the present invention may be tailored to be faster, or to bend more, and to require less voltage than any previously known artificial muscle polymer blend. The muscle material can be configured to any desired shape and dimensions, for use as an implantable device or for external use.

EXAMPLE 1

Preparation of Artificial Muscle Blends

An artificial muscle is prepared by mixing 5 mL deionized water, the desired ratio of aliphatic acid and acrylamide, based on a total monomer content of 2 g, 0.02 g polypyrrole composite with 20% w/w carbon black, 0.02 g N,N'-methylenebisacrylamide, 0.005 g potassium persulfate, 0.005 g sodium metabisulfite and 0.005 g N,N,N,N-tetramethylenediamine (all chemicals were purchased from Aldrich, Milwaukee, Wis.). The mixture is fully blended, and aspirated into a 1 mL syringe or a glass capillary mold, avoiding bubble formation. The artificial muscle samples are cured in a 80° C. air oven and stored at room temperature.

EXAMPLE 2

Preparation of Artificial Muscle Incorporating Different Acrylic Acid Contents Artificial muscles are prepared by mixing 5 mL deionized water, the desired content of acrylic acid, either 45, 57 or 65 wt. %, the analogous amount of acrylamide based on a total monomer content of 2 g, 0.02 g polypyrrole composite doped with 20% w/w carbon black, 0.15 g N,N'-methylenebisacrylamide, 0.05 g potassium persulfate and 0.14 g N,N,N,N-tetramethylenediamine. The artificial muscle samples are cured at 80° C. and then preconditioned in a test solution of 0.15 M NaCl for at least 24 hrs. The increase of the acrylic acid content results in the increase of the response of the artificial muscle showing higher bending angles.

EXAMPLE 3

Preparation of Artificial Muscle Incorporating Different Additive Contents

Artificial muscles are prepared as in Example 2, but using three different additive contents: 0.02 g polypyrrole-carbon black composite (PPY/CB), 0.1 g PPY/CB, and 0.1 g carbon black only, and the muscle serving as the control, where no additive is present. The increase of the PPY/CB content results in the increase of the response of the artificial muscle presenting higher bending angles. When using carbon black alone, the effect is comparatively smaller, while the control shows the smaller response of all, verifying the positive effect of PPy/CB as an additive.

EXAMPLE 4

Preparation of Artificial Muscle Incorporating Different Aliphatic Acids

Three different sets of artificial muscle samples were prepared similar as that in Example 2, but incorporating 0.1 gr PPY/CB and either one of the following unsaturated aliphatic acids: acrylic acid, maleic acid, or glutaconic acid. These 3 different artificial muscle samples were made containing 21 wt. % acrylamide, 4 wt. % PPy/CB composite (5:1), catalyst, accelerator and 64 wt. % of either of the carboxylic acid derivatives acrylic acid, maleic acid or glutaconic acid.

EXAMPLE 5

Preparation of Artificial Muscle Incorporating a Mixture of Different Aliphatic Acids Artificial muscles are prepared as in Example 2, but using a mixture of different aliphatic acids with a preferable total content of 65 wt. %. The artificial muscles are prepared by mixing 4.5 mL deionized water, the desired content of each aliphatic acid used, such as 45 wt. % maleic acid and 20 wt. % acrylic acid, the analogous amount of acrylamide based on a total monomer content of 2 g, 0.1 g polypyrrole composite doped with 20% w/w carbon black, 0.15 g N,N'-methylenebisacrylamide, 500 82 l of the initiator solution containing 0.37 M potassium persulfate and 0.55 M sodium metabisulfite; and 0.14 g N,N,N,N-tetramethylenediamine under continuous mixing and degassing. The artificial muscle samples are cured at 60° C. and then preconditioned in a test solution of 0.15 M NaCl for at least 24 hrs.

EXAMPLE 6

Swelling of Artificial Muscle Samples Placed Parallel to the Electric Field

Figure 6:
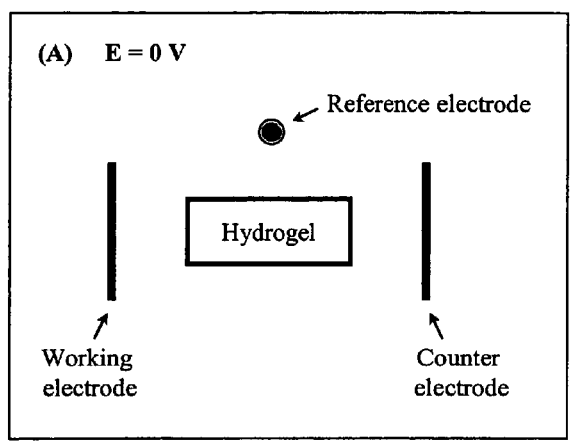
FIG. 6. Electroactuation of an artificial muscle cylindrical sample placed parallel with the electric field. The muscle is placed between two Pt electrode plates in a 150 mM NaCl test solution and a Ag/AgCl electrode is used as the reference electrode (FIG. 6A). The application of the electric field causes the reversible swelling of the muscle side phasing the cathode (FIG. 6B,C).
Figure 6:
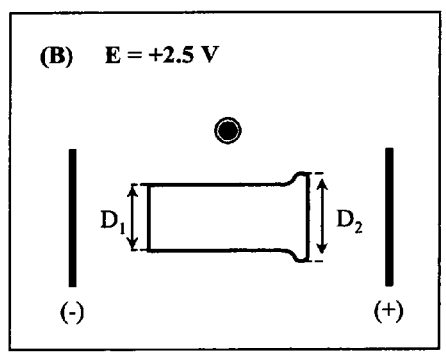
Figure 6:
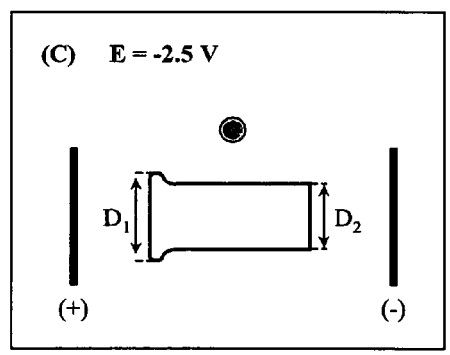

The artificial muscle cylindrical samples obtained as in Example 1 are cut to the desired length for testing. Each test begins by the immersion of the sample in a 150 mM NaCl aqueous solution, between two platinum electrode plates using a Ag/AgCl reference electrode. The sample is placed parallel to the electric field (FIG. 6) that is applied using a BAS 100B/W (Bioanalytical Systems) electrochemical station. First, a constant potential, such as 2.5 V with 1 A current, is applied for 30 min, resulting in the swelling of the muscle side phasing the cathode. Then, the potential is switched to −2.5 V for 30 min causing the reversible swelling on the muscle side phasing now the cathode; while the other side of the muscle, phasing now the anode, returns back to its original dimensions.

EXAMPLE 7

The Artificial Muscle-Based Electroactuated Plunger Valve Model

Figure 7:
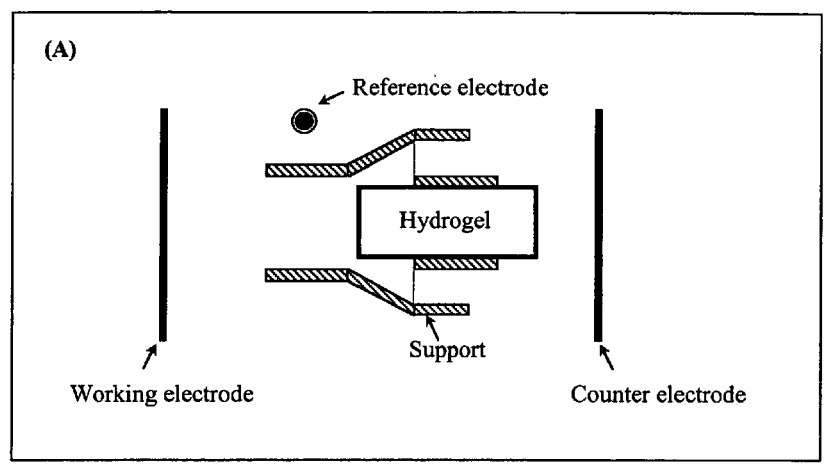
FIG. 7. The use of the artificial muscle sample in a plunger-type configuration, able to fully open and close a reservoir like an on-off valve, is shown. A cylindrical sample of the artificial muscle blend, placed between two Pt electrodes, is fixed in the proximity of a conical tube (FIG. 7A). A Ag/AgCl reference electrode is used, while the whole setup is immersed in the test solution of 150 mM NaCl (FIG. 7A). Under no electroactuation the valve is normally open allowing the flow of fluid through the tube (FIG. 7B). When an electric field is applied, the artificial muscle plunger swells closing any opening of the conical tube, and therefore acting as a closed valve (FIG. 7C).
Figure 7:
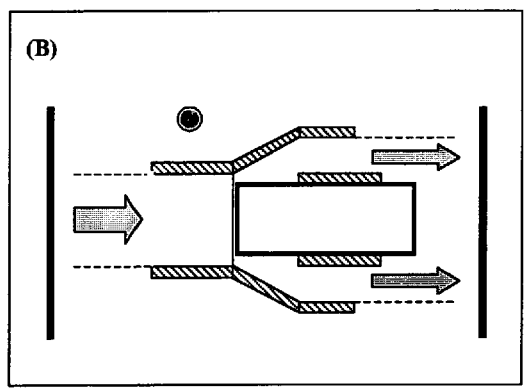
Figure 7:
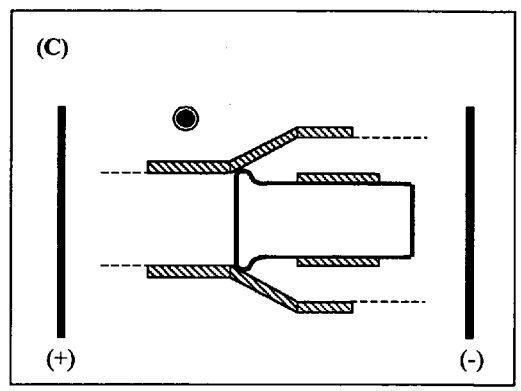

This test is performed to determine whether the artificial muscle works in a plunger-type configuration, i.e., to fully open and close a reservoir like an on-off valve. A cylindrical sample of the artificial muscle blend (Example 1) is placed into a holder and positioned in the proximity of a conical tube as in FIG. 7A. This valve is normally open in the absence of electric field, allowing the flow of fluid through the tube (FIG. 7B). When an electric field is applied, the artificial muscle plunger swells closing any opening of the conical tube, and therefore acting as a closed valve (FIG. 7C). When the polarity of the electrodes change again the artificial muscle plunger shrinks back to its initial diameter, thus opening the valve and permitting again the flow of the fluid. This on/off cycle of the valve configuration of the artificial muscle is shown schematically in FIG. 7.

EXAMPLE 8

Bending of Artificial Muscle Samples Placed Perpendicular to the Electric Field

Figure 8:
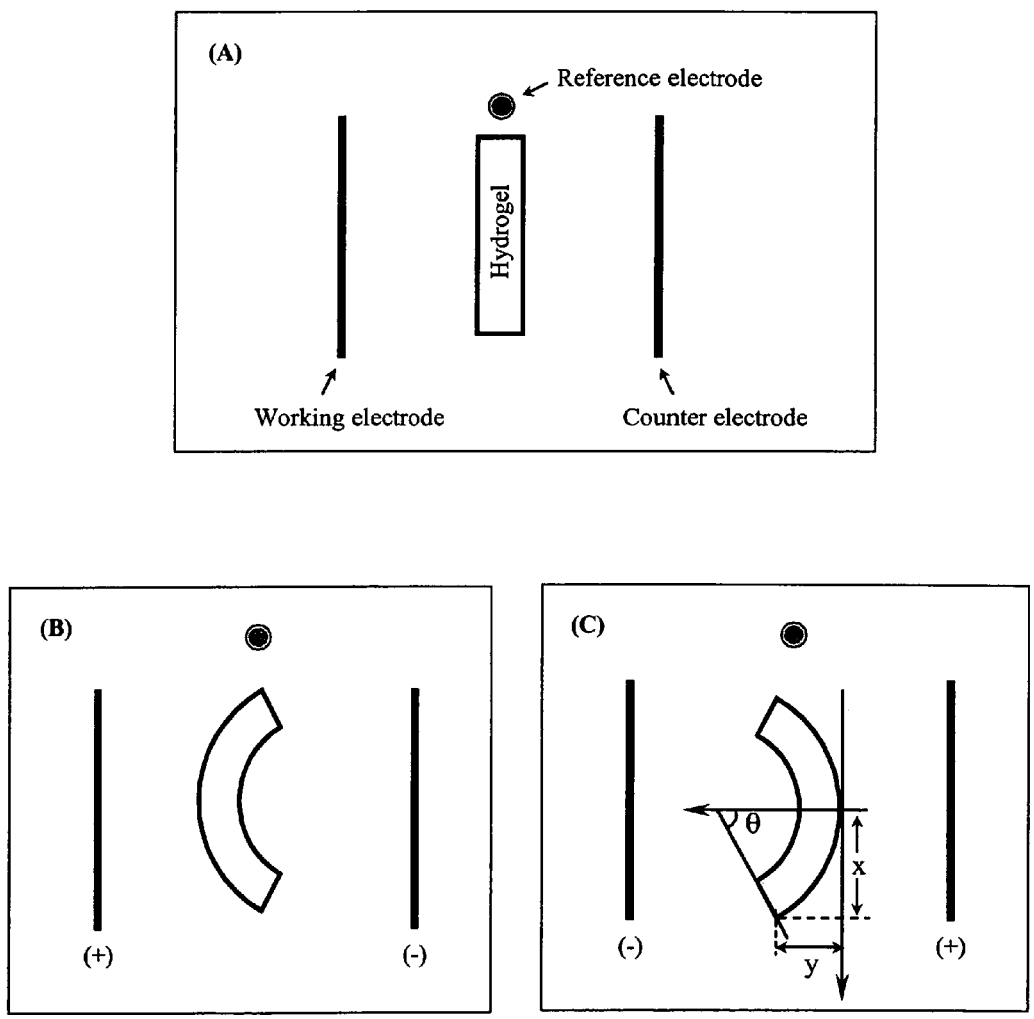
FIG. 8. Electroactuation of an artificial muscle cylindrical sample placed perpendicular with the electric field. The muscle is placed between two Pt electrode plates in a 150 mM NaCl test solution (FIG. 8A), while a Ag/AgCl electrode is used as a reference. The application of the electric field causes the reversible bending of the muscle toward the cathode (FIG. 8B,C).

The artificial muscle cylindrical samples obtained as in Example 2 are preconditioned and cut to the desired length for testing. Each test begins by immersing the sample in a 150 mM NaCl aqueous solution, between two platinum electrode plates, using a Ag/AgCl reference electrode (FIG. 8A). The application of the electric field results in the bending of the artificial muscle toward the cathode (FIG. 8B). When the polarity of the electrodes is changed, the muscle returns back to its original position and bends towards the other electrode (which is now the cathode) as shown in FIG. 8C. The fast and reversible bending response of the artificial muscle, expressed as bending angle, $\theta$, is measured according to the known formula (M. Homma, Y. Seida & Y. Nakano, *J Polym. Sci.*, 2001, 82, 76-80) $\theta=2 \tan^{-1}(y/x)$, (FIG. 8C).

EXAMPLE 9

Bending of Artificial Micromuscle Sample Placed Perpendicular to the Electric Field The actuation characteristics of an artificial micromuscle of the invention having dimensions 400 µm×400 µm×2500 µm are examined. One end of the micromuscle is fixed on a glass support with a droplet of silicone grease, while the other end is free to move under electroactuation. The response of the artificial muscle is visualized and recorded using a Nikon Diaphot 200 inverted microscope and a CCD camera. The applied voltage is first cycled continuously between +1/−1 V with a 200 mV/s scan rate for 12 continuous cycles. FIG. 3 shows the response of the micromuscle, which bends "in tune" with the applied voltage. The application of 1 V with current of 1 A results in the bending of the hydrogel towards the counter electrode (serving as the cathode) with a bending angle of 18°. The cycling of the potential by the application of −1 V results in the return of the muscle to the initial aligned position and further bending towards the opposite direction (towards the working electrode now serving as the cathode) which is denoted by the negative bending angle of −18°. The application of higher potential of 2 and 3 V results in the increase of the response of the material, to the bending angles of 25° and 32°, respectively. In addition, the characteristics of the artificial micromuscle (bending angle and response time) are improved compared to that of the artificial macromuscle, of the same composition and dimensions of 4×10 mm, with bending angle of 23.5° degrees under the application of 3 V for 2 min. Therefore, the response characteristics of the artificial muscle of the invention can be tuned by altering the sample dimensions. It should also be noted that the examined artificial micromuscle behaved properly after 5 months of storage in the test solution, which demonstrates the high storage stability of this material.

EXAMPLE 10

The Artificial Muscle-Based Electroactuated Flap Valve Model

The artificial muscle of the invention is also tested in a flap valve-type configuration. A rectangular artificial muscle sample, with the same composition as in Example 2, is placed inside a rectangular tube, with one side fixed on the wall of the tube, and the other side resting free, slightly bent, on the tube's inner wall, as in the FIG. 1A. When no potential is applied, the flap valve is fully closed, so when the top of the tube is filled with fluid the muscle prevents the liquid flow through the tube. Under the application of an electric field the artificial muscle bends toward the cathode, opening the channel and permitting the flow of fluid (FIG. 1B). When the polarity of the electrodes is reversed, the flap moves back to the original configuration closing the channel and stopping the flow of the fluid. The bending of the artificial muscle under electroactuation is controlled and reversible, therefore permitting the opening and closing of the channel on demand.

EXAMPLE 11

The Artificial Muscle-Based Fluid Release from a Plastic Rigid Reservoir

An artificial muscle sample, with the same composition as in Example 2, is fixed at one end on a support immersed in the test cell, with its flat surface resting on and fully covering the opening of a reservoir filled with fluid (FIG. 5A). The reservoir is normally closed when no voltage is applied, trapping the fluid in the reservoir. Under electroactuation, the artificial muscle bends toward the cathode, uncovering the opening of the reservoir and permitting the fluid release. The artificial muscle is kept electroactuated until the release of the fluid is complete and the reservoir is totally empty (FIG. 5B).

EXAMPLE 12

The Artificial Muscle-Based Fluid Release from a Flexible Semi-Spherical Reservoir An artificial muscle sample, with the same composition as in Example 2, is fixed at one end while immersed in the test cell, with its flat surface resting in the immediate vicinity of a semi-spherical latex reservoir (FIG. 2A,B). A micropipette tip is fixed at the end of a reservoir filled with fluid. No leakage is recorded as long as no voltage is applied. Under electroactuation, the artificial muscle bends toward the cathode, thus slightly pushing onto the flexible reservoir. As a result, the gradual release of fluid (colored fluid is used in this specific case for visualization of the results) from the reservoir tip and its diffusion in the environment is recorded (FIG. 2C). The flow of fluid is stopped when the polarity of the electrodes is reversed. The reversible bending of the artificial muscle of the invention permits the controlled release of fluid from the reservoir with characteristics depending on the electroactuation conditions.

EXAMPLE 13

The Artificial Muscle-Based Microfluidic Displacement Inside a Microchannel

An artificial muscle sample, with the same composition as in Example 2, is used to actuate a mini-reservoir for a nanoliter- and microliter-range release of fluid in a calibrated polymethylmethacrylate microchannel of dimensions 254× 500 µm (FIG. 4A). The artificial muscle is immersed in the test solution of 0.15 M NaCl, with the one end fixed on a support, and the other end placed on the surface of the mini-reservoir filled with fluid and covered with a poly(dimethylsiloxane) membrane. Under electroactuation, the muscle bends and gently presses the flexible membrane that covers the reservoir, thereby releasing fluid into the calibrated microchannel. Each electroactuation of the muscle results in the increase of the volume of the fluid released (which is in the order of microliters), while no fluid release is observed when no potential is applied (FIG. 4B). This experiment demonstrates the ability of the artificial muscle of this invention to be used for the controlled fluid release, for example as a microliter pump.

EXAMPLE 14

The Whiskered Artificial Muscle-Based Fluid Release from a Rigid Mini-Reservoir

Figure 9:
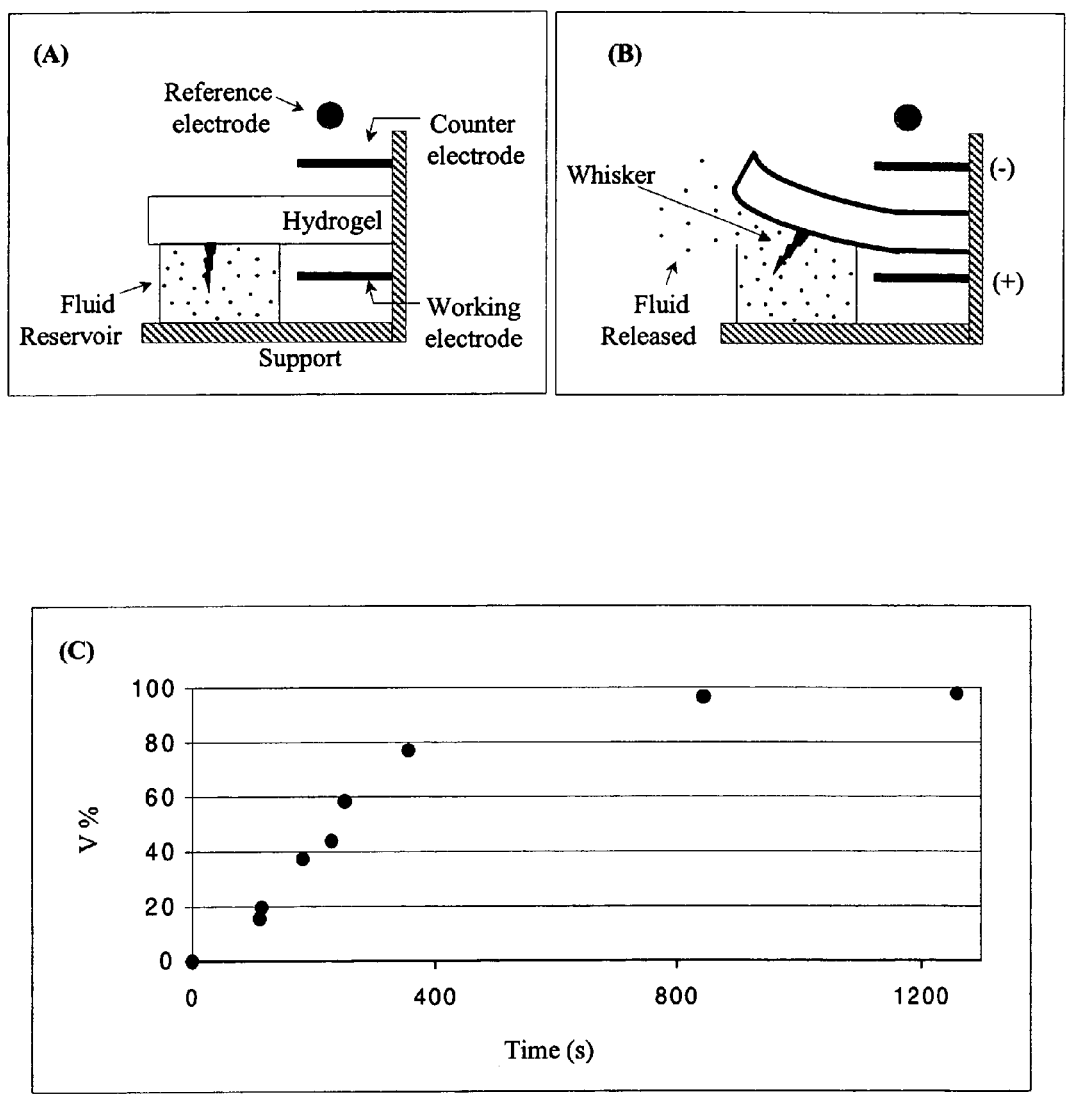
FIG. 9. The application of a whiskered artificial muscle for the fluid release from a reservoir is presented. The whiskered artificial muscle, fixed at one end on a support, is placed between two Pt electrodes, while a Ag/AgCl is used as a reference. The flat surface of the muscle covers the opening of a reservoir filled with fluid (FIG. 9A). The whole setup is immersed in the test solution of 150 mM NaCl. The reservoir is closed when no potential is applied. Under electroactuation, the artificial muscle bends toward the cathode uncovering the opening of the reservoir. The whisker that is attached to the hydrogel and is immersed in the reservoir rises as it follows the movement of the bending muscle, stirring the fluid and increasing the rate of the fluid delivery (FIG. 9B). The shape and size of the whisker is varied according to the shape of the reservoir to maximize the fluid turbulence.

A small plastic whisker is rooted into the flat surface of an artificial muscle, with the same composition as in Example 2. This whiskered artificial muscle is fixed at one end and set in the test cell so that its flat surface rests on and fully covers the opening of a reservoir filled with fluid (FIG. 9A). The reservoir is normally closed when no potential is applied. Under electroactuation, the artificial muscle bends toward the cathode uncovering the opening of the reservoir. At this point, the whisker that is attached to the hydrogel and is immersed in the reservoir, rises as it follows the movement of the bending muscle, stirring the fluid and increasing the rate of the fluid delivery. The shape and size of the whisker can be varied according to the size and shape of the reservoir to maximize the turbulence of the fluid. As seen in FIG. 9C, the delivery of the fluid is complete emptying the reservoir from its contents. A pattern recognition shareware software (posted on the internet by the University of Texas Health Science Service at San Antonio Tex.) is used to quantify the volume released. The fluid released from the reservoir presented in FIG. 9C is determined from the time-based evolution of the two-dimensional black-and-white histograms of the colored fluid as seen in the transparent reservoir.

EXAMPLE 15

Figure 10:
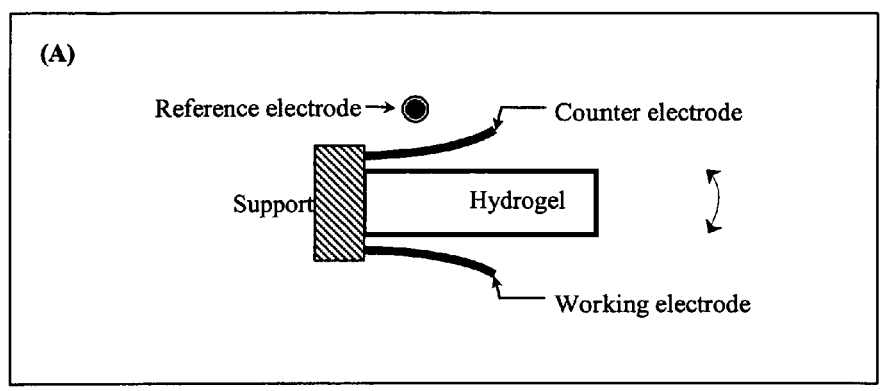
FIG. 10. The bending of the artificial muscle when electroactuated under the application of +/=1 V with 10 mA is demonstrated. The muscle is placed between two gold electrode plates, perpendicular to the electric field, and a Ag/AgCl is used as the reference electrode (FIG. 10A). The setup is immersed in a 150 mM NaCl test solution.
Figure 10:
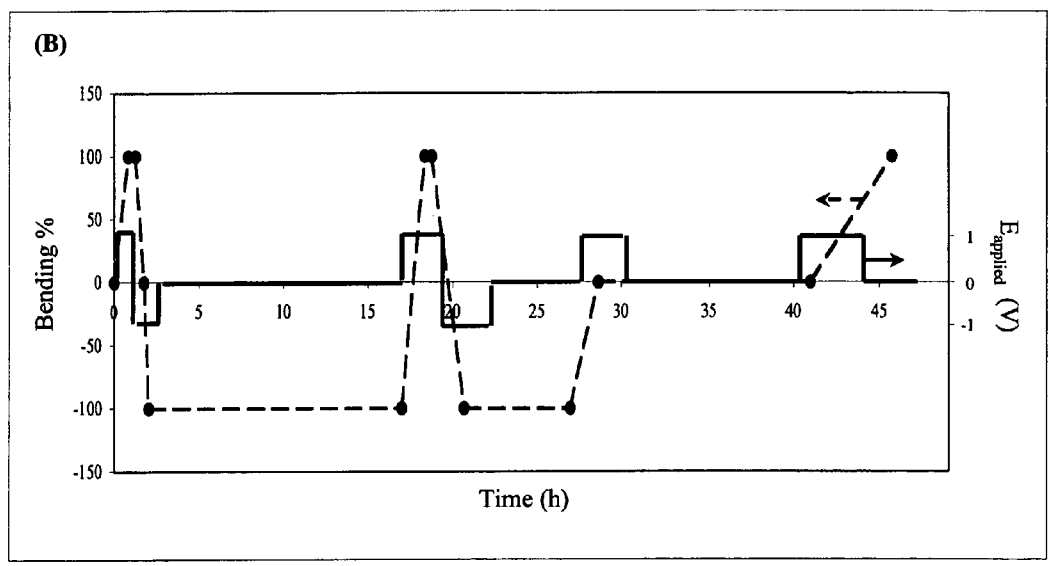

Electroactuation of Artificial Muscle Sample Placed Perpendicular to the Electric Field with 1-2 V at 10 mA Artificial muscle samples obtained as in Example 2 are immersed in a 150 mM NaCl testing solution, between two gold electrode plates, using a Ag/AgCl reference electrode (FIG. 10A). The main purpose of this test is to prove an adequate actuation of the artificial muscle at very low voltage and current. The artificial muscle sample, placed perpendicular to the electric field, bends toward the cathode under electroactuation with a constant voltage of +1 V and current of 10 mA for 60 min. When the voltage is switched to −1 V with 10 mA, the muscle returns to the original position and continues to bend toward the other direction, toward the electrode being now the cathode. In addition to the reversible bending, the artificial muscle can also stay actuated for as long as the electroactuation conditions dictate (in this experiment for the next 17 hours) to meet the requirements of even a long-term fluid delivery. After the long electroactuation to −1V, the potential is switched back to +1 V with 10 mA for the next 2 hours, and the muscle is actuated by bending toward the opposite direction. FIG. 10B shows the reversibility and operational stability of the material for shorter and longer actuation times. This experiment demonstrates the low power demands for the electroactuation of the artificial muscle of the invention and the high reversibility and operational stability of the material.

EXAMPLE 16

Figure 11:
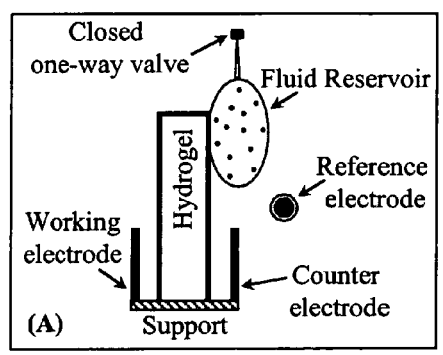
FIG. 11. Fluid release from a flexible reservoir under the electroactuation of an artificial muscle, in setups where the muscle is either a separate component, lying in the vicinity of the reservoir (FIGS. 11A,B), or an intrinsic part of the reservoir (FIGS. 11C,D). In both designs, the reservoir is equipped with a one-way minivalve, so when no electric field is applied the one-way minivalve is closed preventing the leakage of the fluid (FIGS. 11A,C). Under electroactuation, the muscle bends pressing gently the reservoir releasing the fluid (FIGS. 11B and 11D).
Figure 11:
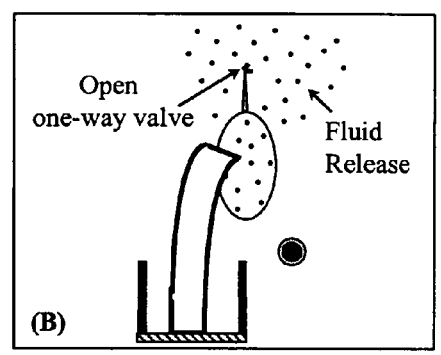
Figure 11:
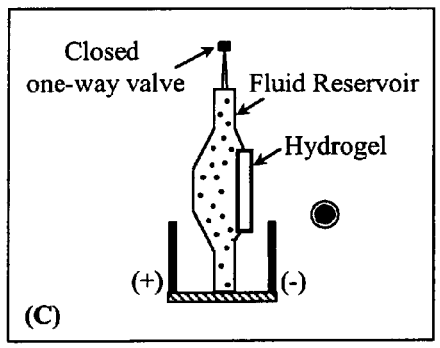
Figure 11:
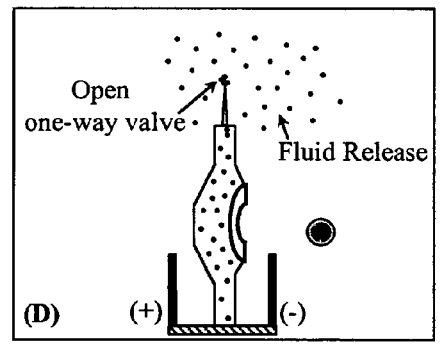

Artificial Muscle-Based Super-Flexible Bladder Fluid Release Device Equipped with a One-Way Minivalve An artificial muscle obtained as in Example 2, is fixed at one end so that its flat surface rests in the immediate vicinity of a reservoir filled with fluid having a one-way minivalve (FIG. 11A). Another embodiment is shown in FIG. 11C, where the artificial muscle is an intrinsic part of the super-flexible bladder, in the form of a strip extending longitudinally from one side of the bladder to the other, in parallel with the two gold electrode plates. In both designs, when no electric field is applied the one-way minivalve is closed, and no fluid leakage occurs. Each time the muscle is electroactuated under +2V with 10 mA, it bends and gently presses the flexible reservoir, thus gradually releasing a thin fluid plume through the one-way valve, which is now open by the applied pressure (FIGS. 11B and 11D). The manner in which the fluid is released and the volume of the fluid delivered depend on the magnitude of the potential applied and the time of the electroactuation.

EXAMPLE 17

Figure 12:
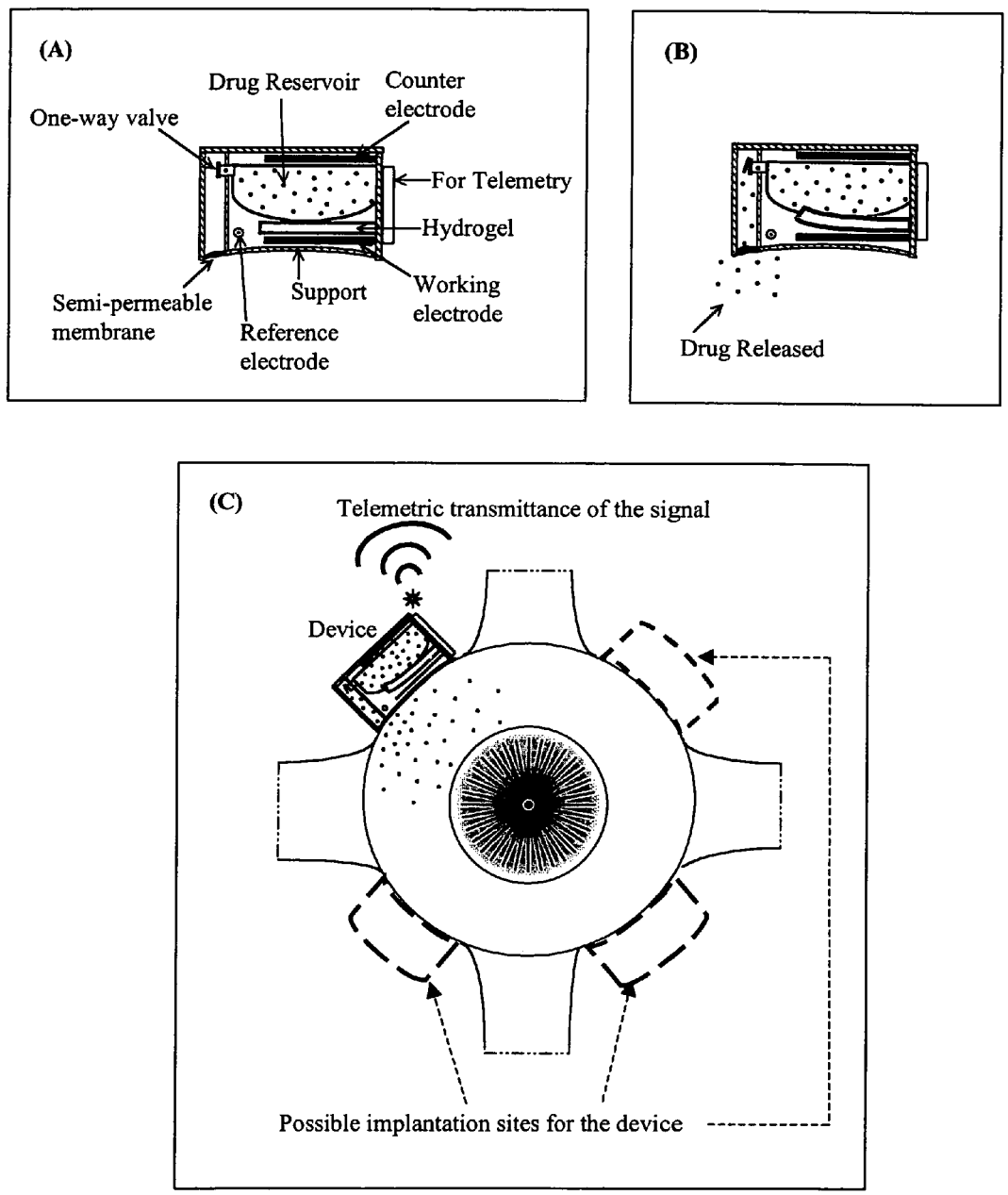
FIG. 12. An application of the artificial muscle-based fluid release device, for the trans-scleral delivery. This device (FIG. 12A) is based on a miniature artificial muscle, which under electroactuation bends, releasing the fluid from a superflexible bladder system equipped with a one-way minivalve (FIG. 12B). The device is enclosed in a biocompatible support equipped with a semi-permeable membrane, for the delivery of the fluid, and a geometry optimized for implantation to an animal or human sclera (FIG. 12C).

The Artificial Muscle-Based Implantable Drug Delivery Device for Trans-Scleral Delivery This device is basically a miniature artificial muscle-based super-flexible bladder system equipped with a one-way minivalve. Its geometry is optimized for the implantation to a rabbit sclera (FIGS. 12A,B). From FIG. 12C, which shows the anatomic relations of rectus extraocular muscle insertions to the corneal limbus (L. Apt & N. B. Call, *Ophthalmic Sugrery and Lasers,* 1982, 13, 2, 108-112) it becomes apparent that there are several implantation sites available. The three-dimensional space available for the device implantation at each site is approximately (3.5 mm×5.4 mm×6.7 mm) for the rabbit eye, and (5 mm×8 mm×10 mm) for the human eye.

What is claimed is:

1. An electroactive hydrogel composition comprising acrylamide; unsaturated aliphatic acid having the formula R=CH—COOH, wherein R is selected from the group consisting of —CH$_2$, —CH—COOH, and —CH—(CH$_2$)$_n$—COOH, where n is an integer, or a combination of these aliphatic acids; a conductive polymer; and at least one cross-linking agent, wherein the hydrogel is electroactive in the absence of contact with electrodes and at a pH range of from about 3 to about 10.

2. The electroactive hydrogel composition of claim 1 wherein the unsaturated aliphatic acid is present in an amount of about 65 wt. %, of the total composition.

3. The electroactive hydro gel composition of claim 2 wherein the unsaturated aliphatic acid is acrylic acid, maleic acid, glutaconic acid, or a mixture thereof.

4. The electroactive hydrogel composition of claim 3 wherein the conductive polymer is a polypyrrole-carbon black composite.

5. The electro active hydrogel composition of claim 4 wherein the polypyrrole-carbon black composite is present in an amount of about 4 wt. % of the total composition.

6. The electroactive hydrogel composition of claim 1 wherein the hydrogel comprises about 65 wt. % acrylic acid.

7. The electroactive hydrogel composition of claim 6 wherein the hydrogel comprises about 4 wt. % polypyrrole/carbon black.

8. The electroactive hydrogel composition of claim 1 further comprising a therapeutic, or diagnostic agent.

9. A drug delivery device for controlled delivery of a therapeutics, diagnostic agent to an animal comprising an electroactive hydrogel composition comprising acrylamide; unsaturated aliphatic acid having the formula R=CH—COOH, wherein R is selected from the group consisting of —CH$_2$, —CH—COOH, and —CH—(CH$_2$)$_n$—COOH, where n is an integer; a conductive polymer; and at least one cross-linking agent, wherein the hydrogel composition is electroactive over a pH range of from about pH 3 to about pH 10, in the absence of contact with electrodes, and in the presence of an electric energy source of from about 1 to about 5 V.

10. The drug delivery device of claim 9 wherein said device is implantable.

11. The drug delivery device of claim 10 wherein the device is a microvalve.

12. The drug delivery device of claim 11 wherein the device further comprises at least one reservoir containing the therapeutic, diagnostic agent, and wherein application of an electric current to the device causes the microvalve to intermittently release the therapeutic, or diagnostic agent from the reservoir.

13. The drug delivery device of claim 9 wherein the unsaturated aliphatic acid comprises preferably about 65 wt. % acrylic acid.

14. The drug delivery device of claim 13 wherein the hydrogel composition comprises preferably about 4 wt. % polypyrrole-carbon black.

15. The drug delivery device of claim 8 wherein the device is implantable.

16. A method for delivering a therapeutic, or diagnostic agent to a patient comprising
 (a) applying on or implanting in the patient a drug delivery device comprising an electroactive hydrogel comprising acrylamide; unsaturated aliphatic acid having the formula R=CH—COOH, wherein R is selected from the group consisting of —CH$_2$, —CH—COOH, and —CH—(CH$_2$)$_n$—COOH, where n is an integer; a conductive polymer; at least one cross-linking agent; and a therapeutic, or diagnostic agent; and
 (b) activating the delivery device by applying a current of 40 mA or less, wherein electroactuation of the hydrogel results in release of the therapeutic agent, agent or diagnostic agent from the drug delivery device.

17. The method of claim 16 wherein the electric field is applied at a predetermined cycle of positive and negative voltage.

* * * * *